(12) United States Patent
Tolson

(10) Patent No.: US 6,217,581 B1
(45) Date of Patent: *Apr. 17, 2001

(54) HIGH PRESSURE CEMENT INJECTION DEVICE FOR BONE REPAIR

(76) Inventor: John Thomas Tolson, 5390 Plum St., Unit 146, Fort Worth, TX (US) 76148

(*) Notice: Subject to any disclaimer, the term of this patent is extended or adjusted under 35 U.S.C. 154(b) by 0 days.

This patent is subject to a terminal disclaimer.

(21) Appl. No.: 09/346,861

(22) Filed: Jul. 2, 1999

Related U.S. Application Data

(63) Continuation-in-part of application No. 08/969,949, filed on Nov. 25, 1997, now Pat. No. 5,928,468, which is a continuation-in-part of application No. 08/544,557, filed on Oct. 18, 1995, now abandoned.

(51) Int. Cl.⁷ .................................................. A61B 17/56
(52) U.S. Cl. .................................. 606/86; 606/92; 606/94
(58) Field of Search ............................... 606/86, 92, 93, 606/94, 95

(56) References Cited

U.S. PATENT DOCUMENTS

| | | | |
|---|---|---|---|
| 131,408 | 9/1872 | Peacock . | |
| 2,040,126 | 5/1936 | Grieve | 144/309 |
| 2,570,588 | 10/1951 | Nylund | 144/309 |
| 3,352,336 | 11/1967 | Smith | 144/310 |
| 3,892,621 | 7/1975 | Salonen | 156/513 |
| 4,132,516 | 1/1979 | Story | 156/94 X |
| 4,338,925 * | 7/1982 | Miller | 606/94 |
| 4,420,358 | 12/1983 | Kindt . | |
| 4,555,286 | 11/1985 | Orisaka et al. | 156/94 |
| 4,576,152 * | 3/1986 | Muller | 606/93 |
| 4,593,685 * | 6/1986 | McKay et al. | 606/94 |
| 4,625,722 * | 12/1986 | Murray | 606/95 |
| 4,627,434 * | 12/1986 | Murray | 606/63 |
| 4,780,162 | 10/1988 | Forler et al. | 156/94 |
| 4,815,454 * | 3/1989 | Dozier, Jr. | 606/94 |
| 4,826,373 | 5/1989 | Nakaro | 411/82 |
| 4,865,229 | 9/1989 | Schneider | 222/325 |
| 4,869,403 | 9/1989 | Bruning | 222/327 |
| 4,976,372 | 12/1990 | Rogers, Jr. | 222/324 |
| 5,115,844 | 5/1992 | Hanson | 144/2 R |
| 5,178,712 | 1/1993 | Sakai et al. | 156/305 X |
| 5,214,987 | 6/1993 | Fenton | 81/460 |
| 5,249,716 | 10/1993 | Sullivan | 282/568 |
| 5,249,899 | 10/1993 | Wilson | 411/82 |
| 5,370,273 | 12/1994 | Rohloff et al. | 222/145 |
| 5,928,468 * | 7/1999 | Tolson | 156/578 |
| 6,045,555 * | 4/2000 | Miller | 606/94 |

OTHER PUBLICATIONS

K–P Manufacturing Co, (Minneapolis) Catalogue Pages Showing Grease Guns n.3–5486–35582 (Page 2); Inflating Needles Part Nos 3197; Grease Fitting 3–5331–35368; Grease Gun Hose & Accessories Part Nos 3–2015–32127.

K–P Manufacturing Co, Minneapolis, Catalogue Published 1984 Pages Showing Grease Guns No. 3–5486–35582 (Page 2); Grease Fitting 3–5331–35368; Grease Gun Hose & Accessories Parts 3–2015–32127.

(List continued on next page.)

Primary Examiner—Gene Mancene
Assistant Examiner—Michael B. Priddy
(74) Attorney, Agent, or Firm—Robert W. J. Usher

(57) ABSTRACT

An adaptor for injecting cement dispensed under high pressure from a cement gun into a bone cavity or into an interstice in a joint formed between a prosthetic pin and cement in the cavity, anchoring the pin in the cavity, to repair the joint has a shank portion with a self tapping external thread tapering from a connecting portion having an internal thread for attachment to a zerk, and radially outward wings, forming fingerpieces by which the shank portion can be rotated. An internal glue passageway extends completely through the adapter. A kit for injecting cement includes two adapters, a zerk, a high pressure lever action hydraulic gun for cement, two flexible connecting hoses, two plugs and a pressure release valve.

4 Claims, 4 Drawing Sheets

OTHER PUBLICATIONS

National Industries Corp., Catalogue (Lowell, Michigan) Published 1984, Inflation Needles Part No. 3197.

KP Manufacturing Co, Minneapolis, Catalogue Published 1984, Page 4 Part Nos 3–1420/2 Grease Injector Needle.

Stryker Instruments (Kalamazoo MI) Catalogue. "High Vacuum Cement Injection System". MI PT No. 1000–119 rev C. (4 pages) Believed Prior Art.

Stryker Instruments (Kalamazoo MI) Catalogue 'Advanced Cement Mixing System' Pt No. 1000–310 Rev B1, (4 pages) Beleived Prior Art.

Stryker Instruments Catalogue. 'Bone Preparation System' BP No. 1000–340 (4 Pages) Believed Prior Art.

* cited by examiner

HIGH PRESSURE CEMENT INJECTION DEVICE FOR BONE REPAIR

RELATED APPLICATIONS

This is a continuation in part of Ser. No. 08/969,949 filed Nov. 25, 1997, issued as U.S. Pat. No. 5,928,468 on Jul. 27, 1999 which is a continuation in part application of Ser. No. 08/544,557 filed Oct. 18, 1995 (abandoned).

FIELD OF THE INVENTION

The invention relates to devices for applying cement under pressure to bone cavities or interstices, for example for treating osteoporosis and to methods for repairing bone prosthesis in situ, particularly artificial hip joints.

BACKGROUND OF THE INVENTION

A conventional technique for treating hip diseased hip joints involves the replacement of the patients diseased hip joint by the substitution of a prosthetic hip joint having a pin which is anchored by cement in the femur cavity to secure the hip joint to the femur. When fitting the joint, the top of the femur in the region of the trabeculae is cut open and the bone marrow removed through the top opening by a scooping and suction technique, emptying the bone cavity or medullary canal for the receipt of the pin and a two-part epoxy cement injected into the cavity through the top opening to spread around the pin using a gun, similar in construction to a caulking gun. Caps of various selected sizes are required to be fitted around the gun nozzle to seal the top opening during injection in an attempt to permit a relatively modest pressure increase to perhaps 2–3 p.s.i. in an attempt to completely fill all interstices around the pin.

However, the pin is made of titanium which is much harder than the cement and as a result of the difference in hardness, after the joint has been in use for a number of years, typically about 10 years, hairline cracks or interstices develop at the interface of the titanium pin and epoxy cement. The conventional remedy has required that the entire joint (pin) be removed and replaced which is effectively a repeat of the earlier procedure which is an undesirable major operation.

It is also known to completely fill a medullary canal with cement through an opening cut in the bone in the upper end for the treatment of osteoporosis.

Examples of devices and mechanisms previously used to instal the artificial joint are described in the catalogue of Stryker Instruments, MI, PT No 1000-119 rev C; PT. NO. 1000-310 REV B1; BP NO 1000-340 for their bone preparation systems, third generation cementing technique and cement injection system.

SUMMARY OF THE INVENTION

It is one object of the invention to provide an apparatus and method which will obviate the requirement to remove and replace the artificial joint as a result of the development of hairline cracks or interstices at the interface of the prosthesis pin and cement.

It is another object of the invention to provide an apparatus and method permitting the injection of the cement at very high pressures into the bone cavity or medullary canal and interstices to ensure maximum intrusion of cement therein.

According to one aspect, the invention provides an adaptor for injecting cement dispensed under high pressure from a cement gun into a bone cavity or into an interstice in a joint formed between a prosthetic pin and cement in the cavity anchoring the pin in the cavity thereby to repair the joint, comprising an elongate body with leading, penetrating and rear, connecting ends, the body having a pointed penetrating shank which tapers outward as it extends rearward from the leading end and is formed with an external self-tapping screw thread and a fingerpiece protruding radially outward adjacent the rear end comprising a pair of wings which protrude forward while diverging in opposite radial directions and an internal cement passageway extending axially completely through the body communicating with leading and rear ends, the rear end being provided with means for attachment to a zerk attached to a cement outlet of the gun so that, with the zerk attached to the rear end, the leading end can be manually screwed into sealing engagement with a bore tapped into the bone and an outlet hose of the cement gun secured to the zerk so that cement dispensed under high pressure from the gun will be injected through the adaptor into the cavity or interstice to fill and seal the interstice securing the pin in the bone cavity.

According to another aspect, the invention provides a kit for injecting cement into a bone cavity or into an interstice in a joint formed between a prosthetic pin and cement in a femur cavity achoring the pin in the cavity thereby to fill the cavity and repairing the joint comprising a hydraulic, trigger action high pressure gun, two flexible hoses, a zerk, two adapters, two plugs and a pressure release valve, each adaptor comprising an elongate body with leading, penetrating and rear, connecting ends, the body having a pointed penetrating shank which tapers outward as it extends rearward from the leading end and is formed with an external screw thread and a fingerpiece protruding radially outward adjacent the rear end and an internal glue passageway extending axially completely through the body communicating with leading and rear ends, the rear end being formed with an internal screw thread for attachment to a zerk so that the adapters with one having a zerk attached to a rear end can be manually screwed into sealing engagement with respective bores tapped into a femur into communication with an interstice therein and the outlet hose of the gun secured to the zerk and the pressure release valve secured between the other adapter and the other hose so that cement dispensed under high pressure from the gun injected through the one adapter into the femur cavity will fill the interstice and seal the joint, with the adapters subsequently unscrewed from the respective bores and the plugs fitted in respective bores to seal the cavity.

The invention includes a method for repairing a hairline crack or interstice in a joint between a prosthetic anchoring pin and a anchoring cement in bone receiving the pin, without removing the pin from the bone and a method for treating osteoporosis in which the marrow is displaced from the medullary canal by injection of cement under high pressure to reinforce the bone.

The screw threaded adaptor and zerk seal against back pressure enabling a lever operated, hydraulic action, gun known for greasing automobiles and which is widely available at low cost to be used for regluing operations to apply glue rapidly under very high pressure (e.g 7,500 psi–10,500 p.s.i.). Furthermore, as the adapters have fingerpieces they may, with zerks attached, readily be screwed by hand into pilot bores tapped in the boney mass Aspects of various devices described herein are described in my application Ser. No. 08/969,949 filed Nov. 25, 1997 which is a continuation in part application of Ser. No. 08/544,557 filed Oct. 18, 1995, the disclosure of which is incorporated herein by reference.

BRIEF DESCRIPTION OF THE DRAWINGS

Specific embodiments of the invention will now be described by way of example only and with reference to the accompanying drawings in which.

DESCRIPTION OF PARTICULAR EMBODIMENTS

Figure 6:
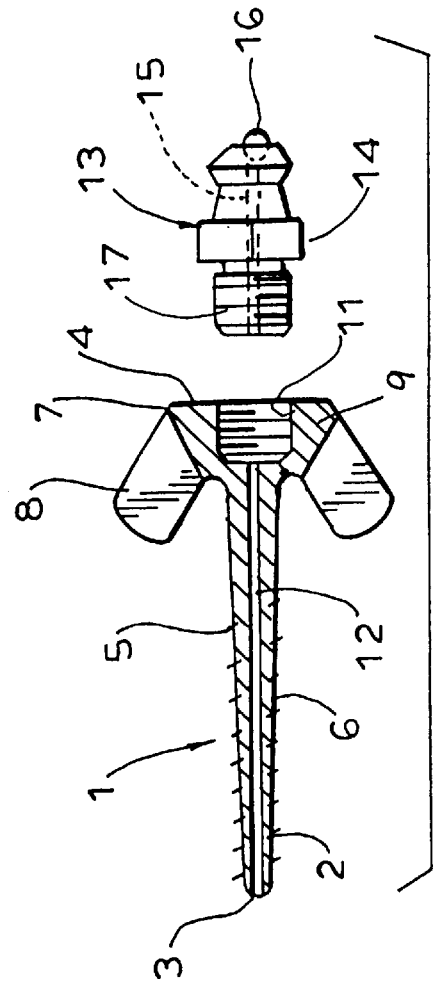

As shown in FIG. 6, and as described in my prior application identified above, the adaptor 1 comprises an elongate, steel body 2 with leading, penetrating and rear, connecting ends, 3 and 4, respectively, and a pointed penetrating shank 5 which tapers outward as it extends rearward from the leading end 3 and is formed with an external, self-tapping screw thread 6. A fingerpiece 7 comprises a pair of wings 8 protruding radially outward and forward from a radially enlarged hub portion 9 having an internal screw thread for attachment to a zerk 11. An axial glue passageway 12 is bored completely through the body so as to communicate with leading and rear ends.

The zerk 13 is of the well known type widely used as a grease nipples and comprises a steel body 14 having a central bore 15 with spring loaded non return ball valve 16 at an inlet end and an externally threaded connecting portion 17 at an outlet end for connection to the adaptor.

The zerk 13 enables connection, via a known pressure adaptor hose 18 and coupler 19, to a high pressure, manually operated, hydraulic action gun 20 widely used for greasing automobiles.

Figure 1:
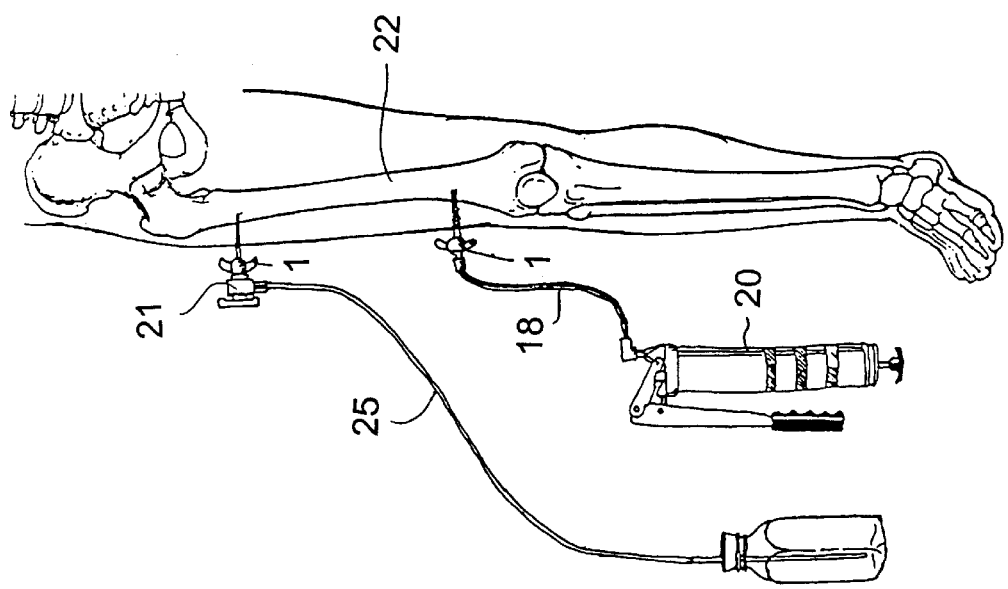
FIG. 1 is a schematic elevational view showing the injection of cement into a person's femur for the treatment of osteoporosis.
Figure 2:
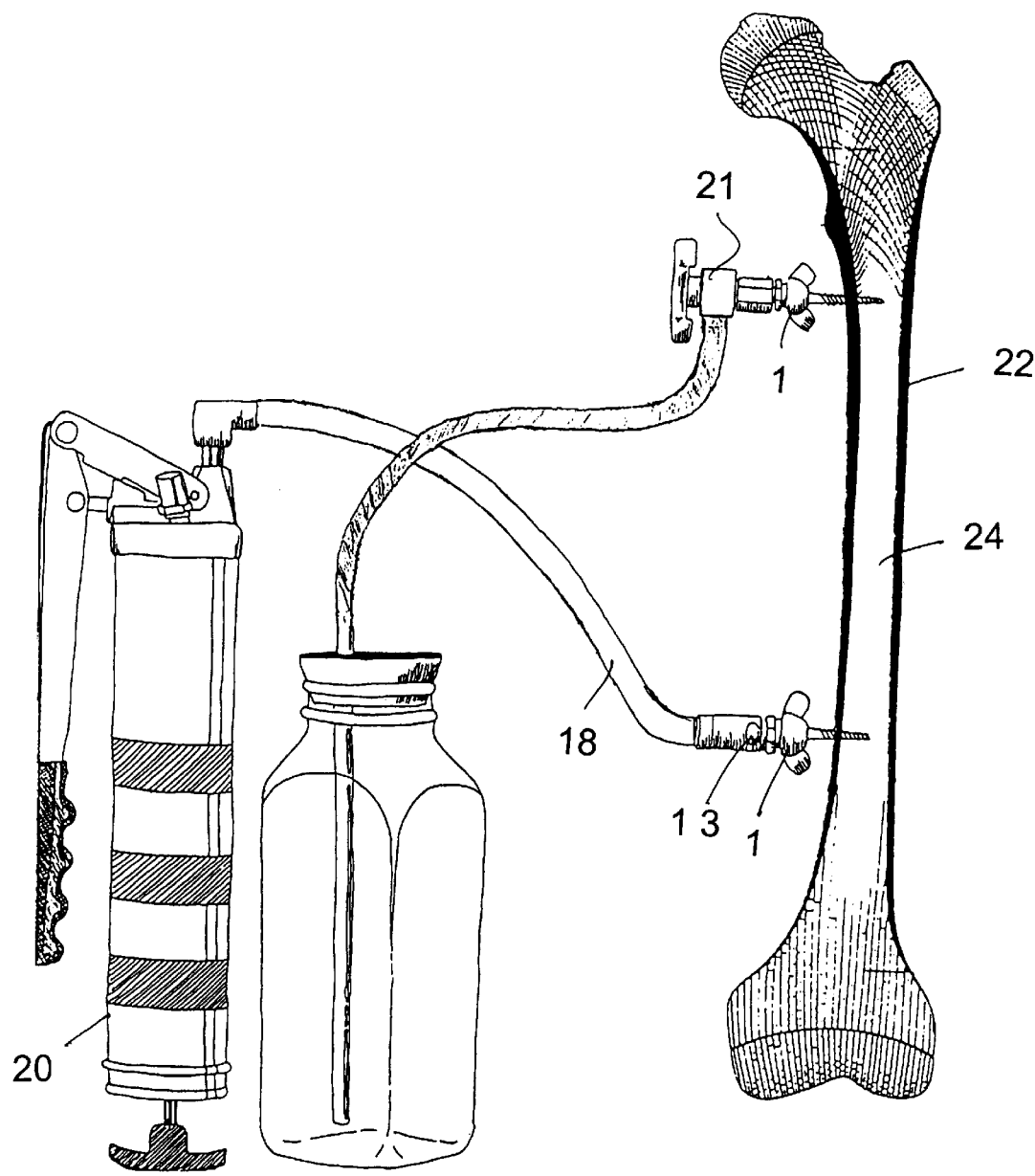
FIG. 2 is an enlarged diagrammatic view of the femur only undergoing cement injection into the medullary canal.

As shown in FIGS. 1 and 2, in a method for treating osteoporosis entry a first adapter 1 with a zerk attached to a rear end and another adaptor 1 with a manual pressure release valve 21 of well known type attached to a rear end are manually screwed into entry and exit bores tapped adjacent lower and upper ends of an affected femur 22 in communication with opposite upper ends of the medulla canal or central bone cavity 24. A pressure hose 18 connects the outlet of the gun 20 to the zerk and another hose 25 connects the outlet of the valve 21 to a collection jar. Suitable premixed epoxy cement is then injected into the medullary canal under high pressure selectively controlled by the valve 21 to advance up the canal displacing the marrow therefrom. The procedure can be monitored by MRI or X-ray to detect the progress of the cement up the canal. Appearance of the cement in the hose will also indicated that the canal is completely full.

The presence of the screw thread on the adaptors, and the provision of the zerk enable injection of cement at very high pressure while the epoxy has flexural characteristics compatible to bone providing good reinforcement with minimal body intrusion.

Figure 3:
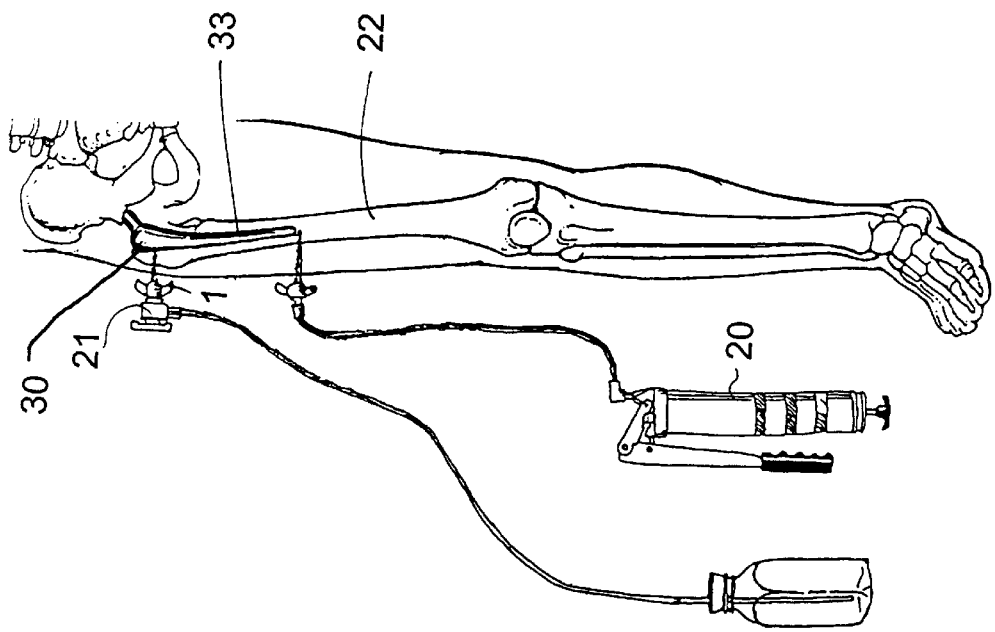
FIG. 3 is a schematic elevation showing the injection of cement into a person's femur for the repair of a prosthesis pin anchoring.
Figure 4:
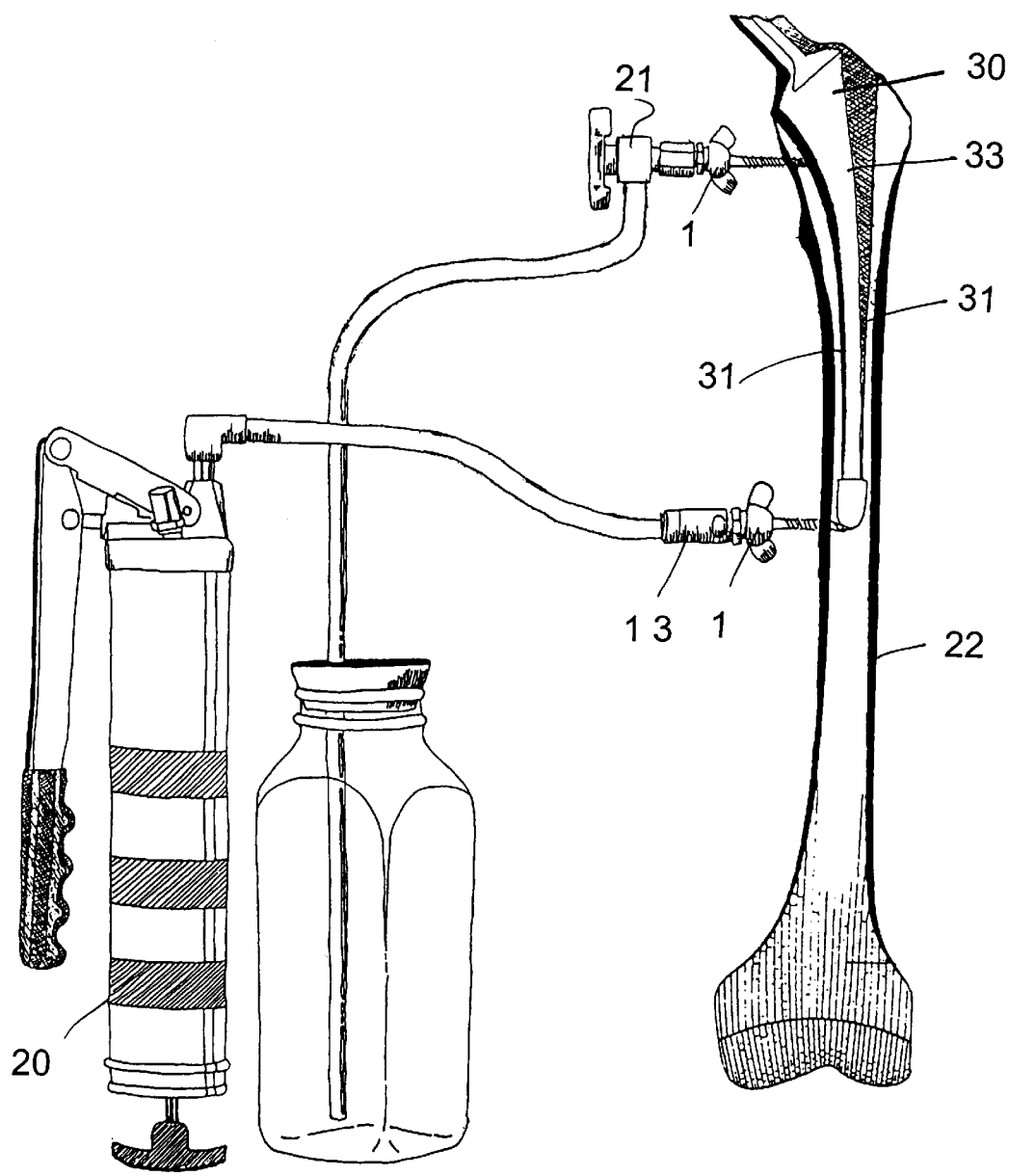
FIG. 4 is an enlarged view of the femur undergoing cement injection for during prosthesis repair.
Figure 5:
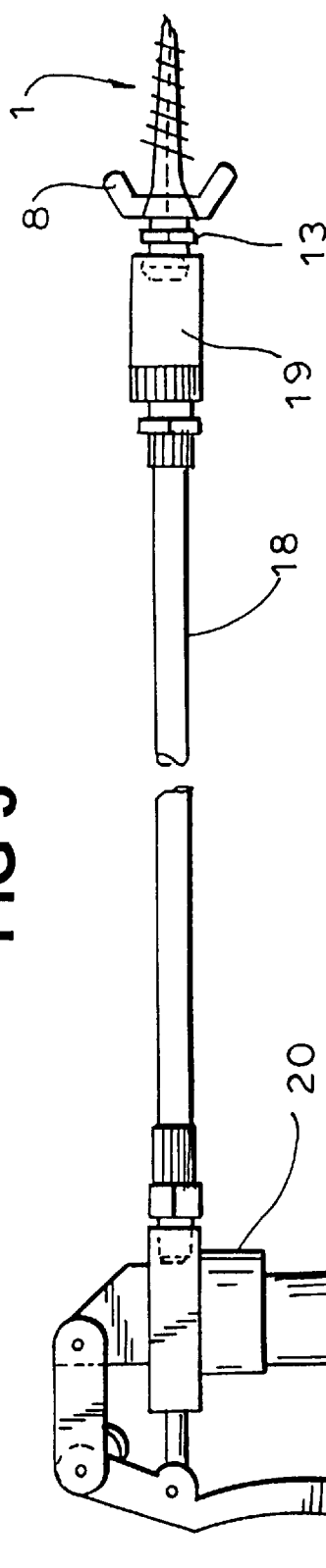
FIG. 5 is an elevational view, of a high pressure gun of known type connected by a flexible hose to a zerk screw-fitted in a rear end of the adaptor; and, FIG. 6 is an elevational view, partly in cross-section, of the adaptor and zerk exploded apart for clarity.

As shown in FIGS. 3 and 4, the procedure for repair of the artificial hip joint 30 by re-cementing a hairline crack 31 or interstice which forms over time around the pin 33 between the surface of the relatively hard titanium pin and the softer epoxy cement is similar, in that entry and exit bores communicating with the interstice are tapped in the boney mass at the lower tip of the pin and adjacent the upper end of the femur. Epoxy cement is then injected therein under the high pressures typical of conventional grease guns, for example, 5,500, 7,500 or 10,500 P.S.I, monitoring the procedure as above, to substantially completely fill, reseal and repair the joint.

Clearly this involves only a minimally invasive procedure obviating the trauma associated with removal and replacement of the prosthesis. It is clearly very much faster and very much less expensive, both in terms of applied cost and materials.

What is claimed is:

1. An adaptor for injecting cement dispensed under high pressure from a cement gun into a bone cavity or into an interstice in a joint formed between a prosthetic pin and cement in the cavity anchoring the pin in the cavity thereby to repair the joint comprising an elongate body with leading, penetrating and rear, connecting ends, the body having a pointed penetrating shank which tapers outward as it extends rearward from the leading end and is formed with an external self-tapping screw thread and a fingerpiece protruding radially outward adjacent the rear end comprising a pair of wings which protrude forward while diverging in opposite radial directions and an internal cement passageway extending axially completely through the body communicating with leading and rear ends, the rear end being provided with means for attachment to a zerk attached to a cement outlet of the gun so that, with the zerk attached to the rear end, the leading end can be manually screwed into sealing engagement with a bore tapped into the bone and an outlet hose of the cement gun secured to the zerk so that cement dispensed under high pressure from the gun will be injected through the adaptor into the cavity or interstice to fill and seal the interstice securing the pin in the bone cavity.

2. A kit for injecting cement into a bone cavity or into an interstice in a joint formed between a prosthetic pin and cement in a femur cavity anchoring the pin in the cavity thereby to fill the cavity and repairing the joint comprising a hydraulic, trigger action grease gun, two flexible hoses, a zerk, two adapters, two plugs and a pressure release valve, each adaptor comprising an elongate body with leading, penetrating and rear, connecting ends, the body having a pointed penetrating shank which tapers outward as it extends rearward from the leading end and is formed with an external screw thread and a fingerpiece protruding radially outward adjacent the rear end and an internal glue passageway extending axially completely through the body communicating with leading and rear ends, the rear end being formed with an internal screw thread for attachment to a zerk so that the adapters with one having a zerk attached to a rear end can be manually screwed into sealing engagement with respective bores tapped into a femur into communication with an interstice therein and one hose connected between an outlet of the grease gun and the zerk and the pressure release valve secured between the other adapter and the other hose so that cement dispensed under high pressure from the gun injected through the one adapter into the femur cavity will fill the interstice and seal the joint, with the adapters subsequently unscrewed from the respective bores and the plugs fitted in respective bores to seal the cavity.

3. In combination, an adaptor for injecting cement dispensed under high pressure from a cement gun into a bone cavity or into an interstice in a joint formed between a prosthetic pin and cement in the cavity anchoring the pin in the cavity thereby to re-cement and repair the joint and a zerk, the adaptor comprising an elongate body with leading, penetrating and rear, connecting ends, the body having a pointed penetrating shank which tapers outward as it extends rearward from the leading end and is formed with an external self-tapping screw thread and a fingerpiece comprising a pair of wings protruding radially outward adjacent the rear end and an internal cement passageway extending axially completely through the body communicating with leading and rear ends, the rear end being provided with an internal screw thread meshing with a complementary thread on the zerk to attach the zerk to the rear end thereof so that, when the zerk is attached to the cement outlet of the cement gun and to the rear end of the adaptor, the leading end can be manually screwed into sealing engagement with a bore tapped into the bone and an outlet hose of the grease gun secured to the zerk so that cement dispensed under high pressure from the gun will be injected through the adaptor filling the interstice, sealing and repairing the joint.

4. A kit for injecting cement dispensed under high pressure into a bone cavity or into an interstice in a joint formed between a prosthetic pin and cement in the cavity anchoring the pin in the cavity thereby to re-cement and repair the joint and comprising a hydraulic, trigger action grease gun operating at between 5000 and 11000 P.S.I.; a flexible outlet hose for the grease gun, a zerk, and at least one adaptor comprising an elongate body with leading, penetrating and rear, connecting ends, the body having a pointed penetrating shank which tapers outward as it extends rearward from the leading end and is formed with an external screw thread and a fingerpiece protruding radially outward adjacent the rear end and an internal cement passageway extending axially completely through the body communicating with leading and rear ends, the rear end being formed with an internal screw thread for attachment to the zerk so that the adapter with a zerk attached to a rear end can be manually screwed into sealing engagement with a bore tapped into a bone joint to be recemented and the outlet hose of the grease gun secured to the zerk and cement dispensed under high pressure from the gun injected through the adapters to the joint to fill and seal the joint, the adapter unscrewed from the bore and the bore fitted with a plug.

* * * * *